(12) United States Patent
Chen et al.

(10) Patent No.: US 11,530,278 B2
(45) Date of Patent: Dec. 20, 2022

(54) DYNAMIC CONTROL OF COLOCALIZATION OF PROTEINS

(71) Applicants: Wilfred Chen, Hockessin, DE (US); Alexander A. Mitkas, Newark, DE (US)

(72) Inventors: Wilfred Chen, Hockessin, DE (US); Alexander A. Mitkas, Newark, DE (US)

(73) Assignee: University of Delaware, Newark, DE (US)

( * ) Notice: Subject to any disclaimer, the term of this patent is extended or adjusted under 35 U.S.C. 154(b) by 36 days.

(21) Appl. No.: 16/751,793

(22) Filed: Jan. 24, 2020

(65) Prior Publication Data
US 2020/0239600 A1 Jul. 30, 2020

Related U.S. Application Data

(60) Provisional application No. 62/796,237, filed on Jan. 24, 2019.

(51) Int. Cl.
| | |
|---|---|
| *C12N 15/11* | (2006.01) |
| *C07K 19/00* | (2006.01) |
| *C12N 9/22* | (2006.01) |
| *C12N 1/20* | (2006.01) |
| *C07D 209/18* | (2006.01) |
| *C07D 403/14* | (2006.01) |
| *C07C 39/19* | (2006.01) |

(52) U.S. Cl.
CPC ............... *C07K 19/00* (2013.01); *C12N 1/20* (2013.01); *C12N 9/22* (2013.01); *C12N 15/111* (2013.01); *C07C 39/19* (2013.01); *C07D 209/18* (2013.01); *C07D 403/14* (2013.01); *C07K 2319/00* (2013.01); *C12N 2310/531* (2013.01)

(58) Field of Classification Search
None
See application file for complete search history.

(56) References Cited

FOREIGN PATENT DOCUMENTS

WO  WO 20201546123  *  7/2020

OTHER PUBLICATIONS

Schneider et al., Nanoscale, vol. 8, pp. 19853-19866, Dec. 2016.*
Green et al., "Ribocomputing Devices for Sophisticated in Vivo Logic Computation", Nature, 548:117-21 (2017).
Sachdeva et al., "In Vivo Co-Localization of Enzymes on RNA Scaffolds Increases Metabolic Production in a Geometrically Dependent Manner", Nucleic Acids Research, 42(14):9473-9503 (2014).
Siu et al, "Synthetic Scaffolds for Pathway Enhancement", Current Opinion in Biotechnology, 36:98-106 (2015).
International Search Report and Written Opinion for International Application No. PCT/US2020/14982, dated May 20, 2020, 17 pages.
Chappell et al., "A Renaissance in RNA Synthetic Biology: New Mechanisms, Applications and Tools for the Future", Current Opinion in Chemical Biology, 28:47-56, (2015).
Chappell et al., "The Centrality of RNA for Engineering Gene Expression", Biotechnology Journal, 8:1379-1395, (2013).
Da Silva et al., "Introduction and Expression of Genes for Metabolic Engineering Applications in *Saccharomyces cerevisiae*", FEMS Yeast Res., 12:197-214 (2012).
Dixon et al., "NanoLuc Complementation Reporter Optimized for Accurate Measurement of Protein Interactions in Cells", ACS Chem. Biol., 11:400-408 (2016).
Eckermann et al., "New Pathway to Polyketides in Plants", Nature, 396:387-390 (1998).
Gasiunas et al., "Molecular Mechanisms if CRISPR-Mediated Microbial Immunity", Cell. Mol. Life Sci., 71:449-465 (2014).
Goyal et al., "Simultaneous Cell Growth and Ethanol Production from Cellulose by an Engineered Yeast Consortium Displaying a Functional Mini-Cellulosome", Microb. Cell Fact., 10:89 (2011).
Haurwitz et al., "Csy4 Relies on an Unusual Catalytic Dyad to Position and Cleave CRISPR RNA", EMBO J., 31(12):2824-2832 (2012).
Horvath et al., "CRISPR/Cas, the Immune System of Bacteria and Archaea", Science, 327:167-170 (2010).
Hoshino, T., "Violacein and Related Tryptophan Metabolites Produced by Chromobacterium Violaceum: Biosynthetic Mechanism and Pathway for Construction of Violacein Core", Applied Microbiology and Biotechnology, 91:1463-1475 (2011).
Jore et al., "Structural Basis for CRISPR RNA-Guided DNA Recognition by Cascade", Nature Structural & Molecular Biology 18(5):529-537 (2011).
Jorgensen et al., "Metabolon Formation and Metabolic Channeling in the Biosynthesis of Plant Natural Products", Current Opinion in Plant Biology, 8:280-291 (2005).

(Continued)

*Primary Examiner* — Richard G Hutson
(74) *Attorney, Agent, or Firm* — RatnerPrestia

(57) ABSTRACT

The present invention provides a method for controlling colocalization of two or more proteins in a cell. The method comprises expressing the proteins, scaffold RNA molecules having binding motifs for the proteins, and a trigger RNA molecule in the cell. In the presence of the trigger RNA molecule, a scaffold may be assembled (ON) by the scaffold RNA molecules via hybridization such that the proteins may be colocalized; or disassembled (OFF) such that the proteins may be separated and not colocalized. The proteins may provide a biological activity when colocalized or not colocalized.

20 Claims, 9 Drawing Sheets

Specification includes a Sequence Listing.

(56) References Cited

OTHER PUBLICATIONS

Kim et al, "Combinatorial Design of a Highly Efficient Xylose-Utilizing Pathway in *Saccharomyces cerevisiae* for the Production of Cellulosic Biofuels", Appl. Environ. Microbiol., 79(3):931-934 (2013).
Lee et al., "Improved Production of L-Threonine in *Escherichia coli* by Use of a DNA Scaffold System", Appl. Environ. Microbiol., 79(3):774-782 (2013).
Machinek et al., "Programmable Energy Landscapes for Kinetic Control of DNA Strand Displacement", J. Nat. Common., 5:5324, 9 pages (2014).
Makarova et al., "An Updated Evolutionary Classification of CRISPR-Cas Systems", Nat. Rev. Microbiol., 13(11):722-736 (2015).
Menard et al., "The Structural and Functional Coordination of Glycolytic Enzymes in Muscle: Evidence of a Metabolon?", Biology, 3:623-644 (2014).
Pitera et al., "Balancing a Heterologous Mevalonate Pathway for Improved Isoprenoid Production in *Escherichia coli*", Metab. Eng., 9:193-207 (2007).
Price et al., "Scaffoldless Engineered Enzyme Assembly for Enhanced Methanol Utilization", Proc. Natl. Acad. Sci. U. S. A., 113(45):12691-12696 (2016).
Qing et al., "Cold-Shock Induced High-Yield Protein Production in *Escherichia coli*", Nat. Biotechnol., 22(7):877-882 (2004).
Rosano et al., "Recombinant Protein Expression in *Escherichia coli*: Advances and Challenges", Front. Microbiol., 5(172):1-17 (2014).
Salvail-Lacoste et al., "Affinity Purification of T7 RNA Transcripts with Homogeneous Ends Using ARiBo and CRISPR Tags", RNA, 19:1003-1014 (2013).
Sashital et al., "An RNA-Induced Conformational Change Required for CRISPR RNA Cleavage by the Endoribonuclease Cse3", J. Nat. Struct. Mol. Biol., 18(6):680-688 (2011).
Saunders et al., "Triacetic Acid Lactone Production in Industrial *Saccharomyces* Yeast Strains", J. Ind. Microbiol. Biotechnol., 42:711-721 (2015).
Semchyshyn, H., "Hydrogen Peroxide-Induced Response in *E. coli* and *S. cerevisiae*: Different Stages of the Flow of the Genetic Information", Cent. Eur. J. Biol., 4(2):142-153 (2009).
Sun et al., "Creation of Artificial Cellulosomes on DNA Scaffolds by Zinc Finger Protein-Guided Assembly for Efficient Cellulose Hydrolysis†", Chem. Commun., 50:1423-1425 (2014).
Westfall et al., "Production of Amorphadiene in Yeast, and Its Conversion to Dihydroartemisinic Acid, Precursor to the Antimalarial Agent Artemisinin", Proc. Natl. Acad. Sci. U. S. A., 109(3):E111-E118 (2012).
International Preliminary Report on Patentability and Written Opinion for International Application No. PCT/US2020/014982, dated Jul. 27, 2021, 7 pages.
Seelig et al., "Enzyme-Free Nucleic Acid Logic Circuits", Science, 314:1585-8 (2006).
Jiang et al., "Real-Time Detection of Isothermal-Amplification Reactions with Termostable Catalytic Hairpin Assembly", J. Am. Chem. Soc. 135:7430-3 (2013).
Chen et al., "Dynamic Protein Assembly by Programmable DNA Strand Displacement", Nat. Chem., download from https://doi.org/10.1038/s41557-018-0016-9, 10 pages (2018).
Carte et al., "CasS Is an Endoribonuclease That Generates Guide RNAs for Invader Defense in Prokaryotes", Genes & Development, 22:3489-3496 (2008).
Carte et al., "Binding and Cleavage of CRISPR RNA by Cas6", RNA, 16:2181-2188 (2010).
Du et al., "Engineering Translational Activators with CRISPR-Cas Sysetm", ACS Synthetic Biology, 5:74-80 (2016).
Green et al., "Toehold Switches: De-Novo-Designed Regulators of Gene Expression", Cell, 159:925-939 (2014).
Niewoehner et al., "Evolution of CRISPR RNA Recognition and Processing by Cas6 Endonucleases", Nucleic Acids Research, 42(2):1341-1353 (2014).
Shao, et al., "Recognition and Cleavage of a Non-Structured CRISPR RNA by Its Processing Endoribonuclease Cas6", Structure, 21(3):385-393 (2013).
Siu et al., Riboregulated Toehold-Gated gRNA for Programmable CRISPR-Cas9 Function, Nature Chemical Biology, 15:217-220, (2019).
Sokolowski et al., "Cas6 Specificity and CRISPR RNA Loading in a Complex CRISPR-Cas System", Nucleic Acids Research, 42(10):6532-6541 (2014).
Srinivas et al., "On the Biophysics and Kinetics of Toehold-Mediated DNA Strand Displacement", Nucleic Acids Research, 41(22):10641-10658 (2013).
Wang et al., "Interaction of the Cas6 Riboendonuclease with CRISPR RNAs: Recognition and Cleavage", Structure, 19(2):257-264 (2011).
Zhang et al., "Control of DNA Strand Displacement Kinetics Using Toehold Exchange", J. Am. Chem. Soc., 131:17303-17314 (2009).

\* cited by examiner

Assembly

Disassembly

| Construct name | Hybridization length (nt) | # of turns of RNA | Orientation of proteins |
|---|---|---|---|
| scCR_13 | 13 | 1 | Cis |
| scCR_19 | 19 | 1.5 | Trans |
| scCR_26 | 26 | 2 | Cis |

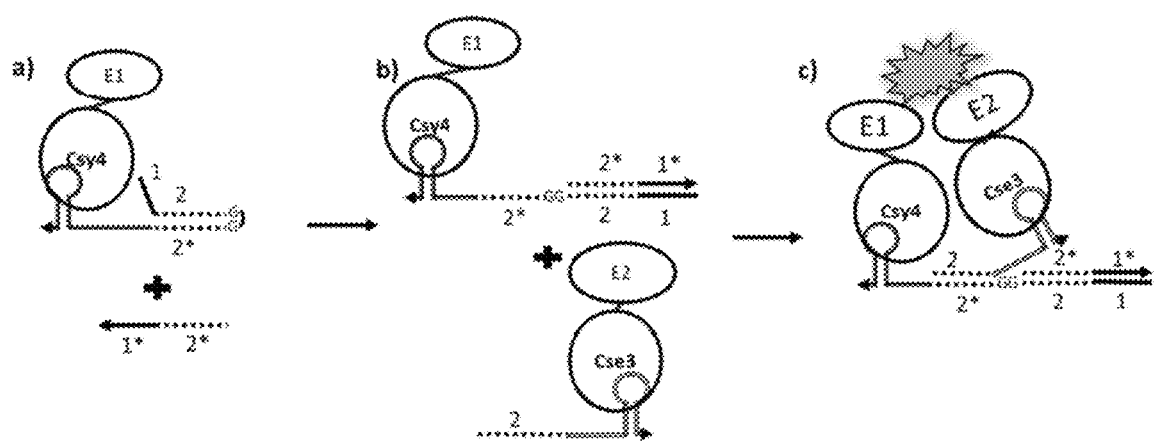

DYNAMIC CONTROL OF COLOCALIZATION OF PROTEINS

CROSS-REFERENCE TO RELATED APPLICATION

This application claims priority to U.S. Provisional Application No. 62/796,237, filed Jan. 24, 2019, the contents of which are incorporated herein by reference in their entireties for all purposes.

REFERENCE TO U.S. GOVERNMENT SUPPORT

This invention was made with government support under Grant No. MCB1543838 and MCB1615731 from the National Science Foundation. The United States has certain rights in the invention.

The Sequence Listing for this application is labeled "UOD-512US_SequenceListing.txt" which was created on Feb. 24, 2020 and is 841 Bytes. The entire content of the sequence listing is incorporated herein by reference in its entirety.

FIELD OF THE INVENTION

The invention relates to colocalization of proteins in cells via scaffold RNA molecules having complementary sequences, especially proteins capable of providing a biological activity when colocalized or not colocalized depending on the nature of the interaction between the proteins.

BACKGROUND OF THE INVENTION

Through metabolic engineering, microorganisms have been engineered to produce high-value chemicals ranging from biofuels to pharmaceuticals. Traditionally, production of non-native molecules has been achieved by a two-step process: (a) introduce a heterologous metabolic pathway into a model organism, such as E. coli and S. cerevisiae, and (b) control the metabolic flux through the non-native pathway through genetic insertions, substitutions, and deletions to regulate enzyme expression. Simple introduction of the enzymes in a metabolic pathway of interest through genetic vectors has been successful for molecules such as small chain hydrocarbons. However, tedious and often unrewarding optimization of the turnover and expression rates of the introduced enzyme is often required to minimize the stress the new pathway inflicts on the model organism.

Precise organization of enzymes through metabolons, which are temporary structures that spatially organize enzymes in the same metabolic pathway, allows for metabolic flux control without changing enzyme activities or expression levels. Native cell metabolons increase the turnover rate of metabolic pathways or help facilitate protein signaling. In plants, they allow the formation of isoprenoids and other products with toxic intermediates, while in muscle tissue they can direct glycolysis. The assembly of the metabolon, typically found on intracellular and plasma membranes, enables substrate channeling (FIG. 1), which allows the product of one enzyme to be quickly processed by the downstream enzymes, due to the proximity of the enzymes. Through their self-assembly, metabolons provide an alternate means of facilitating the up-/and downregulation of native metabolic pathways beyond altering the expression level or turnover rate of the enzymes involved.

The above concept has been successfully taken to create synthetic metabolons that enhance overall yields of multi-enzyme systems through clustering and scaffolding using a combination of nucleic acids and/or proteins as platforms. For example, enhanced in vitro cellulose hydrolysis through the assembly of artificial cellulosomes on DNA scaffolds using zinc finger proteins (ZFPs) and cohesion/dockerin pairs has been demonstrated. Furthermore, the latter scaffold has also been applied in conjunction with a yeast consortium by displaying the synthetic cellulosome on its surface. This consortium achieved 87% of the theoretical yield of ethanol production and a threefold increase in ethanol production over yeast consortia lacking the synthetic cellulosome. Recently, this co-localization concept was also applied to an in vivo process to enhance methanol to methane conversion with great success. All of these concepts highlight the importance of proximity to the overall efficiency of synthetic metabolons.

Despite their success, current synthetic metabolons still lack the ability to dynamically dis-/assemble on cue. While synthetic metabolons optimize product yield, they offer little or no control over the metabolic flux distribution after they have been formed. Without any dynamic control of scaffold dis-/assembly, the scaffold can only redirect metabolic fluxes once, after it assembles the first time. Native metabolons have feedback loops that trigger their dis-/assembly based on intracellular cues, such as substrate, cofactor, or product concentration. The extra control layer in native metabolons helps prevent substrate depletion or product accumulation and is absent from the current static synthetic metabolons used.

There remains a need for a dynamic, modular, high binding affinity scaffold for colocalization of proteins and control of biological activities, for example, intracellular metabolic flux.

SUMMARY OF THE INVENTION

The present invention relates methods for controlling colocalization of two or more heterologous proteins via scaffold RNA molecules in cells.

A method for controlling colocalization of a first heterologous protein with a second heterologous protein in a cell is provided. The method comprises expressing the first heterologous protein and a first scaffold RNA molecule in the cell, wherein the first scaffold RNA molecule comprises a first binding motif, a hybridization sequence and a toehold sequence, the first heterologous protein is bound to the first binding motif, and the first hybridization sequence is bound to a first sequence complementary with the hybridization sequence. The method further comprises expressing the second heterologous protein and a second scaffold RNA molecule in the cell, wherein (i) the second scaffold RNA molecule comprises a second binding motif and the first sequence complementary with the hybridization sequence, the second protein is bound to the second binding motif, whereby the first heterologous protein is colocalized with the second heterologous protein in the cell, or (ii) the second scaffold RNA molecule comprises a second binding motif and a second sequence consisting of a polynucleotide sequence identical to the hybridization sequence, the second protein is bound to the second binding motif, and the first scaffold RNA molecule further comprises the first sequence complementary with the hybridization sequence, whereby the first heterologous protein is not colocalized with the second heterologous protein in the cell. The method further comprises expressing a trigger RNA molecule in the cell, wherein the trigger RNA molecule comprises a first trigger sequence complementary with the toehold sequence and a second trigger sequence complementary with the hybridization sequence, the second trigger sequence complementary with the hybridization sequence, whereby the first trigger sequence complementary with the toehold sequence is bound to the toehold sequence, the first sequence complementary with the hybridization sequence is separated from the hybridization sequence, and the second trigger sequence complementary with the hybridization sequence is bound to the hybridization sequence, and (I) where the second scaffold RNA molecule comprises the first sequence complementary with the hybridization sequence, the first heterologous protein is not colocalized with the second heterologous protein in the cell, or (ii) where the first scaffold RNA molecule comprises the first sequence complementary with the hybridization sequence, the second sequence consisting of a polynucleotide sequence identical to that of the hybridization sequence is bound to the first sequence complementary with the hybridization sequence, and the first heterologous protein is colocalized with the second heterologous protein in the cell.

The first heterologous protein and the second heterologous protein may be different, and the first binding motif and the second binding motif may be different.

The first heterologous protein and the second heterologous protein may be expressed under the same promoter.

Each of the first binding motif and the second binding motif may have a hairpin sequence. The hairpin sequence may consist of 25-35 nucleotides. The hairpin sequence may consist of 30 nucleotides.

The cell may be selected from the group consisting of *E. coli*, *S. cerevisiae*, and HeLa cells.

The method may further comprise expressing a combined scaffold RNA molecule in the cell, and cleaving the combined scaffold RNA to generate the first scaffold RNA molecule and the second scaffold RNA molecule in the cell.

The second scaffold RNA molecule may comprise the first sequence complementary with the hybridization sequence. When the second scaffold RNA molecule comprises the first sequence complementary with the hybridization sequence, the method may further comprise expressing a third heterologous protein and a third scaffold RNA molecule in the cell. The third scaffold RNA molecule may comprise a third binding motif and a third sequence consisting of a polynucleotide sequence identical to that of the hybridization sequence, and the third protein may be bound to the third binding motif. As a result, the first sequence complementary with the hybridization sequence may be bound to the third sequence consisting of a polynucleotide sequence identical to that of the hybridization sequence, and the second heterologous protein may be colocalized with the third heterologous protein.

The first scaffold RNA molecule may comprise the first sequence complementary with the hybridization sequence.

The first heterologous protein and the second heterologous protein may provide a biological activity in the cell when the first heterologous protein is colocalized with the second heterologous protein, and the biological activity may be reduced when the first heterologous protein is not colocalized with the second heterologous protein.

The first heterologous protein and the second heterologous protein may provide a biological activity in the cell when the first heterologous protein is not colocalized with the second heterologous protein, and the biological activity may be reduced when the first heterologous protein is colocalized with the second heterologous protein.

The first heterologous protein may be a first fusion protein of a first enzyme and a first binding protein capable of binding to the first binding motif, and the second heterologous protein may be a second fusion protein of a second enzyme and a second binding protein capable of binding to the second binding motif. The first enzyme and the second enzyme may provide a biological activity in the cell when the first heterologous protein is colocalized with the second heterologous protein, and the biological activity may be reduced when the first heterologous protein is not colocalized with the second heterologous protein. Each of the first binding protein and the second binding protein may be selected from the group consisting of Csy4 from *P. aeruginosa*, Cse3 from *E. coli*, Cse3 from *T. thermophilus*, and Cas6 from *P. furiosus*. The cell may produce a metabolite, and the production of the metabolite by the cell may be increased when the first protein and the second protein are colocalized and reduced when the first protein and the second protein are separated. The metabolite may be selected from the group consisting of indole-3-acetic acid, trans-resveratrol, and violacein. Each of the first enzyme the second enzyme may be selected from the group consisting of Tryptophan-2-monooxygenase (IaaM), Indoleacetamide hydrolase (IaaH), 4-coumarate ligase (4CL), Stilbene synthase (STS), Violacein synthase (VioC), Protodeoxyviolaceinate monooxygenase (VioD), and Violacein biosynthesis protein VioE.

The first heterologous protein may be a first fusion protein of a first enzyme and a first binding protein capable of binding to the first binding motif, and the second heterologous protein may be a second fusion protein of a second enzyme and a second binding protein capable of binding to the second binding motif. The first enzyme and the second enzyme may provide a biological activity in the cell when the first heterologous protein is not colocalized with the second heterologous protein, and the biological activity may be reduced when the first heterologous protein is colocalized with the second heterologous protein. Each of the first binding protein and the second binding protein may be selected from the group consisting of Csy4 from *P. aeruginosa*, Cse3 from *E. coli*, Cse3 from *T. thermophilus*, and Cas6 from *P. furiosus*.

The cell may produce a metabolite. The production of the metabolite by the cell may be increased when the first protein and the second protein are colocalized and reduced when the first protein and the second protein are separated. The metabolite may be selected from the group consisting of indole-3-acetic acid, trans-resveratrol, and violacein. Each of the first enzyme and the second enzyme may be selected from the group consisting of Tryptophan-2-monooxygenase (IaaM), Indoleacetamide hydrolase (IaaH), 4-coumarate ligase (4CL), Stilbene synthase (STS), Violacein synthase (VioC), Protodeoxyviolaceinate monooxygenase (VioD), and Violacein biosynthesis protein VioE.

BRIEF DESCRIPTION OF THE DRAWINGS

FIG. 14 illustrates scaffold assembly upon addition of a trigger strand.

FIG. 15 illustrates a regular trigger, a scrambled toehold trigger and a fully scrambled trigger.

DETAILED DESCRIPTION OF THE INVENTION

The present invention relates to methods for controlling colocalization of two or more proteins via RNA scaffold systems. The invention is especially useful for proteins that interact with each other or are involved in the same biological pathway in the fields of, for example, metabolic engineering and synthetic biology. Genetic circuitry developed using methods of the present invention from synthetic biology helps control the metabolic flux in cells in order to maximize titer product and maximize cell viability. The scaffolds developed according to this invention may be used to colocalize various proteins, for example, ranging from reporter systems to nonnative metabolic pathway proteins, and improve titers in a variety of small molecule chemicals.

Figure 1:
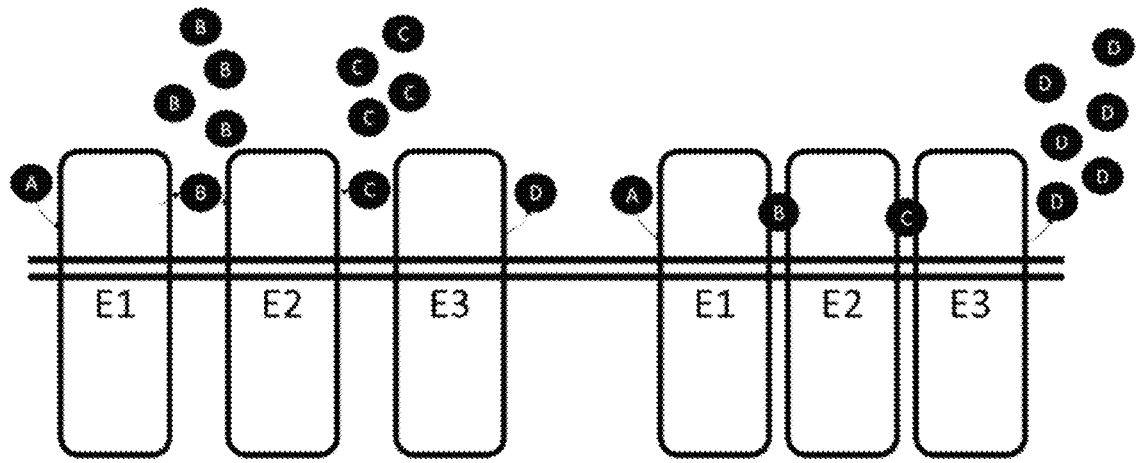
FIG. 1 is an illustration of the concept of substrate channeling. When enzymes E1, E2, and E3 are in close proximity, i.e., colocalized, the flux through the metabolic pathway as a whole increases significantly compared to when they are not colocalized.
Figure 2:
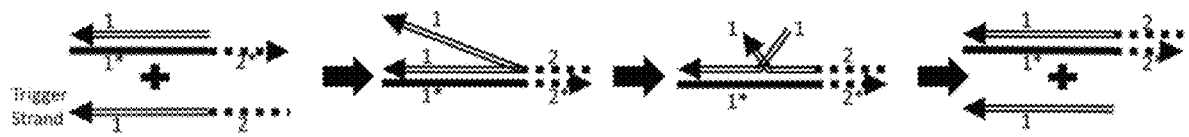
FIG. 2 illustrates one embodiment of toehold mediated strand displacement (TMSD) according to the invention in four drawings from left to right. The first drawing shows a complex, in which a top strand comprises Sequence 1 and a bottom strand comprises Sequence 1* and Sequence 2* at the 3' end of Sequence 1*, and a trigger strand comprising Sequence 2 and Sequence 1 at the 3' end of Sequence 2. Sequence 2* is a toehold region. Sequence 1* in the bottom strand is complementary with and hybridizes to Sequence 1 in the top strand. Sequence 2* is complementary to Sequence 2. The second drawing shows initiation of TMSD by hybridization of Sequence 2 in the trigger strand to Sequence 2* in the bottom strand. The third drawing shows that TMSD continues with hybridization of Sequence 1 in the Trigger Sequence to Sequence 1* in the bottom strand. The fourth drawing shows complete TMSD of the top strand by the trigger strand. The arrows represent the 3' end of each strand.
Figure 3:
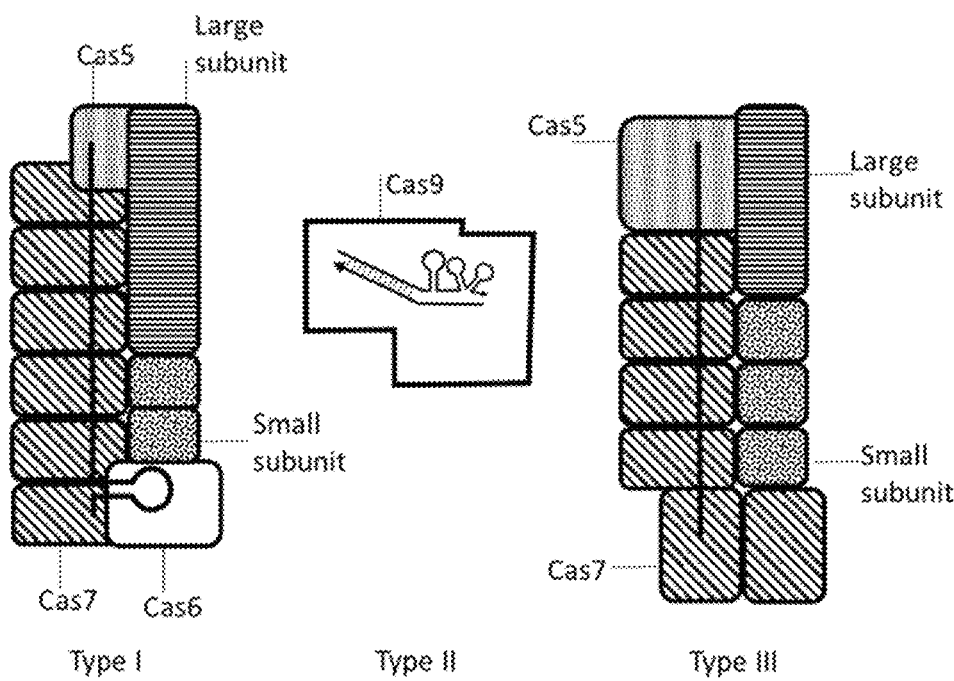
FIG. 3 illustrates a variety of Cas proteins. (a) Type 1 CRISPR/Cas systems. Cas 6 processes long RNA to small crRNA and triggers complex formation. (b) Type II CRISPR/Cas systems. Hybridization of tracrRNA and crRNA to each other allows Cas9 to bind to the complex and identify target DNA sequences. (c) Type III CRISPR/Cas system. Cas5 processes RNA to crRNA and triggers complex formation. Cas6 protein from the CRISPR/Cas Type I family is one of the smaller proteins and exemplified in examples 1, 2, 6 and 7.

The inventors have surprisingly discovered methods for assemble or disassemble a scaffold for controlling colocalization of two Cas6 fusion proteins through hybridization by two RNA strands having complementary sequences and bound specifically to the two Cas6 and/or through toehold mediated strand displacement (TMSD). Proteins having high binding affinities to specific RNA sequences and de novo designed scaffold RNA molecules comprising such specific RNA sequences have been prepared for controlling colocalization of the proteins in vivo and providing biological activity due to colocalization of the proteins. The scaffold may dynamically assemble and bring the fusion proteins of interest, in proximity, for example, within 5-10 nm. Once the scaffold has assembled, the disassembly may be triggered through TMSD, a technology that allows for displacing one DNA or RNA strand in favor of a new trigger strand. The displacement may be facilitated by the presence of an unhybridized 6-12 nucleotide long toehold region at the end of one of the initially hybridized strands. The toehold region provides a foothold onto which the trigger strand can begin to hybridize on. Eventually, the trigger strand may completely hybridize with the toehold strand, essentially kicking out the second strand. The mechanism of TMSD is illustrated in FIG. 2.

TMSD is an excellent candidate for facilitating the dynamic disassembly of the scaffold because its kinetics occurs in the order of minutes to hours. Furthermore, the kinetics can be fine-tuned by altering the length of the toehold and/or by introducing mismatched base pairs in the toehold region. Overall, the scaffold components, which are proteins bound to RNA molecules, may dynamically assemble through strand complementarity of the RNA molecules and, then, dynamically disassemble by the addition/ production of a trigger strand. Although initially the trigger strand may most likely be synthetic, in the long run it is desirable that the trigger strand is under control of a native cell response (for example, low glucose levels or a stress response) so that dissociation of the scaffold may be controlled by cellular responses.

To have a scaffold that dis-/assembles based on hybridization and TMSD, proteins having a high binding affinity, for example, $K_D$ in the range of 1-100 pM, 25-75 pM, or 45-55 pM, that can strongly bind to specific RNA sequences are desirable. To this end, the Cas6 family of proteins may be the second component of the scaffold system. The CRISPR/Cas defense system is a combination of proteins and RNA that functions as the immune system of prokaryotic cells. There are three families of CRISPR/Cas systems: Type I, Type II, and Type III systems (FIG. 2). Although Cas9 is the prevalent protein used in research, the Type I Cas6 proteins are better suited for the proposed dynamic scaffold system. The Cas6 family of proteins are small size (~24 kDa) endoribonucleases that bind in a sequence specific manner to short RNA loop structures (20-30 bp) and cleave at the 3' end of the loop. Each of the Cas6 proteins has a unique binding motif. However, some Cas6 (from the same CRISPR/Cas Type I subtype) proteins' binding motifs have sequence similarity or homology. It is advisable to avoid using two Cas6 proteins that have respective binding motifs with sequence complementarity greater than 70%, 75% 80%, 85%, 90% or 95% to avoid crosstalk in scaffold assembly. Discovered Cas6 proteins and their corresponding binding sequences include Csy4 from *P. aeruginosa*, Cas6 from *P. furiosus*, Cse3 from *E. coli*, and another Cse3 from *T. thermophilus*. The Cas6 proteins have been exemplified for this invention.

Cas6 proteins may be preferable to Cas9, because they as well as their RNA binding motifs are much smaller than their Cas9 analogs. Each of the scaffold components should be as small as possible to minimize steric hindrances when enzymes of interest are fused to them. The small size of the Cas6 proteins may also reduce the risk of TMSD not occurring due to the protein complexes blocking the toehold region. Cas6 proteins have the potential to be fused to large proteins, as it has already been demonstrated that maltose binding protein (MBP) fusions to Cas6 are possible. All Cas6 proteins also have high binding affinities, with their dissociation constants ($K_D$) being in the pM range. High binding affinity is desired to ensure that the scaffold will not randomly begin to dissociate after it is formed. Using Cas6 proteins ensures that the only way scaffold components may dissociate is through specific technology such as TMSD. Cas6 proteins allow dynamic scaffold assembly to be controlled purely by the RNA components due to their high binding affinity and are proven functional fusion partners.

Figure 4:
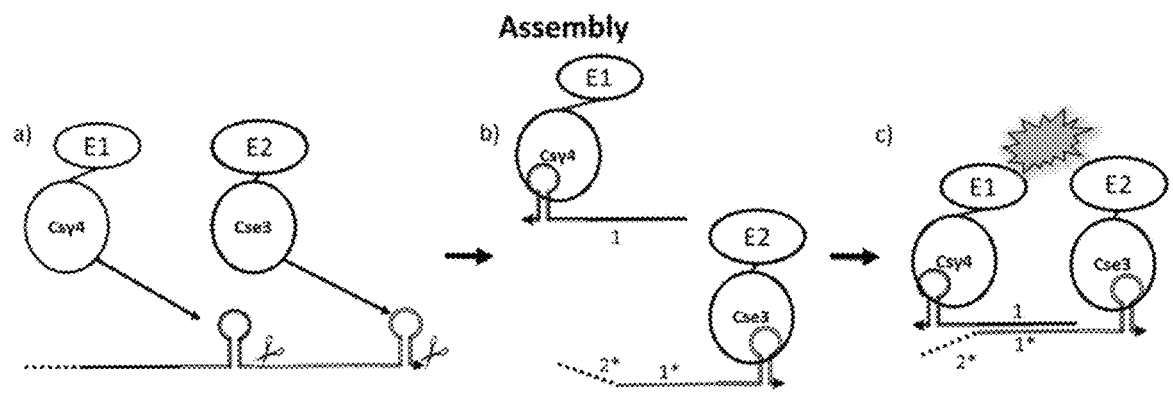
FIG. 4 shows scaffold assembly and colocalization of proteins of interest E1 and E2. (a) E1 and E2 are fused to Csy4 and Cse3 to generate fusion proteins Csy4-E1 and Cse3-E2, respectively. The orthogonal Cas6 proteins Csy4 and Cse3 bind to their respective RNA binding motifs in a single RNA strand and process the single RNA strand by cleaving on the 3' end of their respective binding motifs. (b) After the single RNA strand is processed into two scaffold RNA molecules bound to Csy4-E1 or Cse3-E2, and the 5' complementary regions 1 and 1* of the two scaffold RNA molecules are now free to hybridize. (c) A final scaffold is formed and E1 and E2 are colocalized. 2* represents a toehold that can initiate TMSD.
Figure 5:
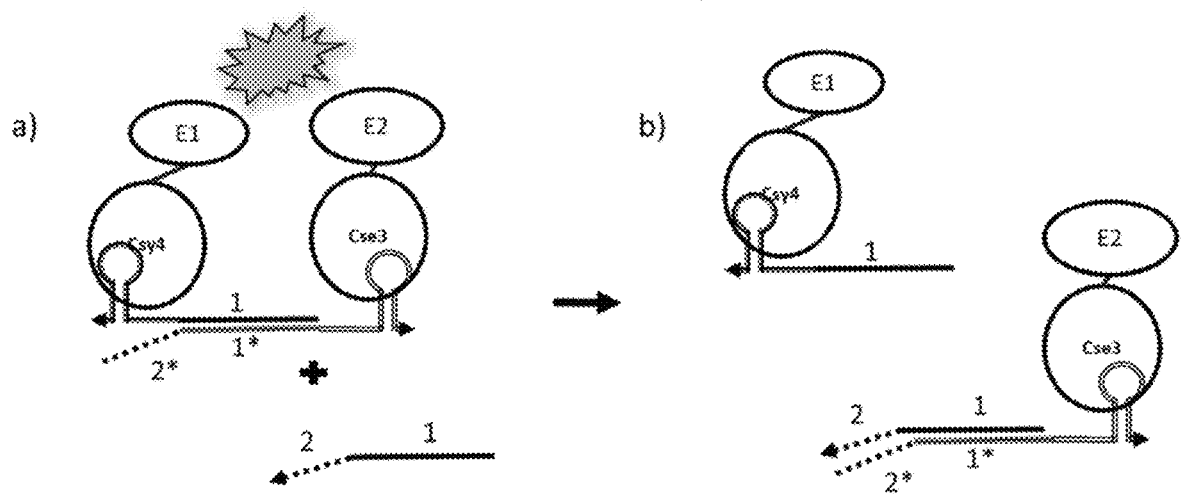
FIG. 5 shows disassembly of the assembled scaffold and separation of colocalized proteins of interest E1 and E2 upon addition of a trigger strand. The trigger strand induces TMSD, which results in separation of colocalized Csy4-E1 and Cse3-E2.

Each of the aforementioned Cas6 proteins binds to a specific sequence, with minimal crosstalk. Their high orthogonality ensures that specific scaffold RNA-Cas6 pairs can be made. The orthogonality, coupled with the Cas6 proteins' ability to cleave RNA strands, makes it possible for multiple orthogonal Cas6 proteins to bind specifically to their respective Cas6 binding motifs in a single large scaffold RNA molecule having the multiple Cas6 binding motifs and 5' extended regions, and cleave the single large scaffold RNA molecule into multiple scaffold pieces capable of spontaneously hybridize and assemble a scaffold (FIG. 4). The 5' extension sequences may control scaffold dis-/assembly based on strand hybridization and TMSD. In designing the 5' extension sequences (that hybridize with each other) the following may be taken into consideration: The length of the hybridization region may not be too long, and may have 13-26 nucleotides. The sequence may not form a secondary structure on its own, and may not interfere with the binding motif it is connected to in any way. By combining all of the RNA scaffold sequences in one large RNA strand, the dynamic assembly of the scaffold may be induced by triggering the expression of the large RNA strand.

The terms "complementary with," "complementary sequences" or "sequence complementarity" as used herein refers to two nucleotide sequences having at least 70%, 75% 80%, 85%, 90%, 95% or 99%, or 100% matching nucleotides (i.e., G-C or A-T for DNA sequences, or G-C or A-U for RNA sequences).

The term "binding specifically" or "specific binding" as used herein refers to binding of a protein to a predetermined polynucleotide sequence (e.g., a binding motif), which may be a DNA or RNA sequence, but not a similar polynucleotide sequence having at least 70%, 75%, 80%, 85%, 90%, 95% or 99% homology to the predetermined polynucleotide sequence.

The present invention provides a first method for controlling colocalization of two proteins in a cell. According to the first method, two proteins are colocalized in a scaffold assembled by two scaffold RNA molecules comprising complementary sequences and binding motifs for the two proteins, and then separated from each other after the scaffold is disassembled by toehold mediated strand displacement (TMSD).

The first method comprises expressing a first protein and a first scaffold RNA molecule in the cell. The first scaffold RNA molecule comprises a first binding motif, a hybridization sequence and a toehold sequence. The first protein is bound to the first binding motif. The toehold sequence may be adjacent to the hybridization sequence. For example, the toehold sequence may be within 0-5 nucleotides from the hybridization sequence. The toehold sequence may be at the 5' end or 3' end of the hybridization sequence. The first binding motif may be at the 5' end or 3' end of the hybridization sequence and the toehold sequence.

The first method also comprises expressing a second protein and a second scaffold RNA molecule in the cell. The second scaffold RNA molecule comprises a second binding motif and a second sequence. The second protein binds to the second binding motif. The second sequence is complementary with the hybridization sequence in the first scaffold RNA molecule and bound to the hybridization sequence in the first scaffold RNA molecule. As a result, the first and second scaffold RNA molecules assemble a scaffold via hybridization between the hybridization sequence in the first scaffold RNA molecule and the second sequence in the second scaffold RNA molecule, and the first protein is colocalized with the second protein in the cell.

The first method further comprises expressing a trigger RNA molecule in the cell. The trigger RNA molecule comprises a first trigger sequence and a second trigger sequence. The first trigger sequence is complementary with the toehold sequence in the first scaffold RNA molecule. The second trigger sequence is complementary with the hybridization sequence in the first scaffold RNA molecule. As a result, the first trigger sequence is bound to the toehold sequence via hybridization, the second sequence in the second RNA molecule is separated from the hybridization sequence, and the second trigger sequence is bound to the hybridization sequence. In other words, the trigger RNA molecule displaces the second scaffold RNA molecule, the scaffold is disassembled, and the first and second proteins are separated from each other and no longer colocalized.

The first method may further comprise expressing a combined scaffold RNA molecule in the cell, and cleaving the combined scaffold RNA to generate the first scaffold RNA molecule and the second scaffold RNA molecule in the cell.

The first method may further comprise expressing a third heterologous protein and a third scaffold RNA molecule in the cell. The third scaffold RNA molecule may comprise a third binding motif and a third sequence. The third protein may be bound to the third binding motif. The third sequence may consist of a polynucleotide sequence identical to that of the hybridization sequence. As a result, the second sequence in the second scaffold RNA molecule may be bound to the third sequence, the second and third scaffold RNA molecules may assemble a scaffold, and the second protein may be colocalized with the third protein.

The present invention also provides a second method for controlling colocalization of two proteins in a cell. According to the second method, the two proteins are separated from each other because two scaffold RNA molecules having complementary sequences and binding motifs for these two proteins are prevented from assembling a scaffold, and then become colocalized after a scaffold is assembled by the two scaffold RNA molecules due to toehold mediated strand displacement (TMSD).

The second method comprises expressing a first protein and a first scaffold RNA molecule in the cell. The first scaffold RNA molecule comprises a first binding motif, a hybridization sequence, a first sequence complementary with the hybridization sequence and a toehold sequence. The first protein is bound to the first binding motif. The hybridization sequence is bound to the first sequence complementary with the hybridization sequence. The toehold sequence may be adjacent to the hybridization sequence. For example, the toehold sequence may be within 0-5 nucleotides from the hybridization sequence. The toehold sequence may be at the 5' end or 3' end of the hybridization sequence. The first binding motif may be at the 5' end or 3' end of the hybridization sequence and the toehold sequence.

The second method also comprises expressing a second protein and a second scaffold RNA molecule in the cell. The second scaffold RNA molecule comprises a second binding motif and a second sequence. The second protein binds to the second binding motif. The second sequence consists of a polynucleotide sequence identical to the hybridization sequence. As a result, the first and second scaffold RNA molecules are prevented from assembling a scaffold via hybridization because the hybridization sequence is bound to the first sequence complementary with the hybridization sequence, and the first protein is not colocalized with the second protein in the cell.

The second method further comprises expressing a trigger RNA molecule in the cell. The trigger RNA molecule comprises a first trigger sequence and a second trigger sequence. The first trigger sequence is complementary with the toehold sequence in the first scaffold RNA molecule. The second trigger sequence is complementary with the hybridization sequence in the first scaffold RNA molecule. As a result, the first trigger sequence is bound to the toehold sequence via hybridization, the first sequence complementary with the hybridization sequence in the first RNA molecule is separated from the hybridization sequence, the second trigger sequence is bound to the hybridization sequence, and the second sequence in the second scaffold RNA molecule is bound to the first sequence complementary with the hybridization sequence in the first scaffold RNA molecule such that a scaffold is assembled by the first and second scaffold RNA molecules. In other words, the trigger RNA molecule displaces the first sequence complementary with the hybridization sequence in the first RNA molecule such that the first RNA molecule becomes available to assemble a scaffold with the second RNA molecule via hybridization between the hybridization sequence in the first scaffold RNA molecule and the second sequence in the second scaffold RNA molecule, and the first protein is colocalized with the second protein in the cell.

The second method may further comprise expressing a combined scaffold RNA molecule in the cell, and cleaving the combined scaffold RNA to generate the first scaffold RNA molecule and the second scaffold RNA molecule in the cell.

According to the invention, the first and second proteins may be different and the first and second binding motifs may be different. The molar ratio of the first protein to the second protein may be in the range from 10:1 to 1:10, from 5:1 to 1:5, or from 2:1 to 1:2. The first and second proteins may be expressed under the same promoter. The first protein and/or the second protein may be heterologous to the cells.

The first binding protein may bind specifically to the first binding motif. The first protein may have a high binding affinity for the first binding motif having, for example, $K_D$ in the range of 1-100 pM, 25-75 pM, or 45-55 pM.

The second binding protein may bind specifically to the second binding motif. The second protein may have a high binding affinity for the second binding motif having, for example, $K_D$ in the range of 1-100 pM, 25-75 pM, or 45-55 pM.

The third binding protein may bind specifically to the third binding motif. The third protein may have a high binding affinity for the third binding motif having, for example, $K_D$ in the range of 1-100 pM, 25-75 pM, or 45-55 pM.

Each protein may comprise a binding domain capable of binding specifically to a binding motif. The binding domain may be from a Cas6 protein, for example, Csy4 from *P. aeruginosa*, Cse3 from *E. coli*, Cse3 from *T. thermophilus*, and Cas6 from *P. furiosus*.

The scaffold RNA molecule may not have a sequence that interferes with the specific binding of a protein to its binding motif (e.g., Cas6 binding motif) in the scaffold RNA molecule. Other than the binding motif, the scaffold RNA molecule may not have a sequence capable of forming a secondary structure, for example, stem-loop structures or pseudoknots, on its own. The hybridization region may consist of 10-30 or 13-26 nucleotides.

The two binding motifs may not have sequence homology greater than 70%, 75%, 80%, 85%, 90% or 95%. Each binding motif may have a hairpin sequence. The hairpin sequence may consist of 20-40, 25-35 or 28-32 nucleotides. For example, the hairpin sequence may be GTTCACTGCCGTATAGGCAGCTAAGAAA (SEQ ID NO: 1), GAGTTCCCCGCGCCAGCGGGGATTAAACCG (SEQ ID NO: 2), or GGATCGATAC-CACCCCGAAGAAAAGGGGACGAGAAC (SEQ ID NO: 3).

The cell may be selected from the group consisting of bacterial, yeast, and mammalian cells. In one embodiment, the cell is E. coli. In another embodiment, the cell is S. cerevisiae.

According to the present invention, the two proteins may provide a biological activity when the two proteins are colocalized or separated. Depending on the nature of the relationship between the two proteins, the biological activity may be increased or decreased when the two proteins are colocalized. In one embodiment, the first protein and second protein provide a biological activity in the cell when the first protein is colocalized with the second protein, and the biological activity is reduced when the first protein is not colocalized with the second protein. In another embodiment, the first protein and the second protein provide a biological activity in the cell when the first protein is not colocalized with the second protein, and the biological activity is reduced when the first protein is colocalized with the second protein.

Each of the two proteins may be a fusion protein of an enzyme and a binding protein. For example, the first protein may be a first fusion protein of a first enzyme and a first binding protein capable of binding to the first binding motif while the second protein may be a second fusion protein of a second enzyme and a second binding protein capable of binding to the second binding motif. The first enzyme and the second enzyme may provide a biological activity in the cell when the first protein is colocalized with the second protein, and the biological activity may be reduced when the first protein is not colocalized with the second protein. Alternatively, the first enzyme and the second enzyme may provide a biological activity in the cell when the first protein is not colocalized with the second protein, and the biological activity may be reduced when the first protein is colocalized with the second protein. Each binding protein may be a Cas6 protein, for example, Csy4 from P. aeruginosa, Cse3 from E. coli, Cse3 from T. thermophilus, and Cas6 from P. furiosus. Each binding protein may be capable of binding specifically to a binding motif. The first and second binding motifs may not have sequence homology greater than 70%, 75%, 80%, 85%, 90% or 95%.

The cell may produce a metabolite, and the production of the metabolite by the cell may be increased when the first and second proteins are colocalized and reduced when the first and second proteins are not colocalized. The metabolite may be selected from the group consisting of indole-3-acetic add, trans-resveratrol, and violacein. The first and second enzymes may be selected from the group consisting of Tryptophan-2-monooxygenase (IaaM), Indoleacetamide hydrolase (IaaH), 4-coumarate ligase (4CL), Stilbene synthase (STS), Violacein synthase (VioC), Protodeoxyviolaceinate monooxygenase (VioD), and Violacein biosynthesis protein VioE.

The scaffold assembly or disassembly may be detected by conventional techniques known in the art. Scaffold assembly involving two proteins bound to two scaffold RNA molecules having complementary sequences may be detected based on co-immunoprecipitation of the two proteins or a biological effect (e.g., emission of luminescence) triggered by colocalization of the two proteins. For example, a small 6×his tag may be attached to one protein and a small FLAG tag to the other. Then, immunoprecipitation using an anti-his tag antibody may be performed. Once the scaffold is assembled by two scaffold RNA molecules having complementary sequences and the binding motifs for the two proteins, both proteins would be pulled out via immunoprecipitation. The presence of the second protein may be visualized via SDS-PAGE gel and/or a western blot probing for the presence of a FLAG tag.

The scaffold may be designed to cycle dynamically between ON (assembled) and OFF (disassembled) states. In many cases of non-native metabolite production, substrate depletion and/or toxic product accumulation can lead to unwanted cell death. The proposed scaffold would minimize the occurrence of these problems by cycling dynamically through ON and OFF states. When the conditions are favorable for metabolite production, the assembly of the scaffold will be triggered. When a metabolite imbalance arises (substrate depletion or product accumulation), the scaffold disassembly is triggered, thus allowing the cell to return to its normal operating levels. The metabolite imbalances may be detected by using engineered promoter systems designed to be activated or repressed in the presence or absence of the substrate or product. The expression of the trigger strand may be paced under control of the aforementioned engineered promoter thus controlling when the scaffold assembles or disassembles through metabolite concentration. The proposed dynamic cycling will allow for higher product titer and more efficient resource usage by the cells in the culture.

Example 1. In Vitro Scaffold Assembly

Figure 6:
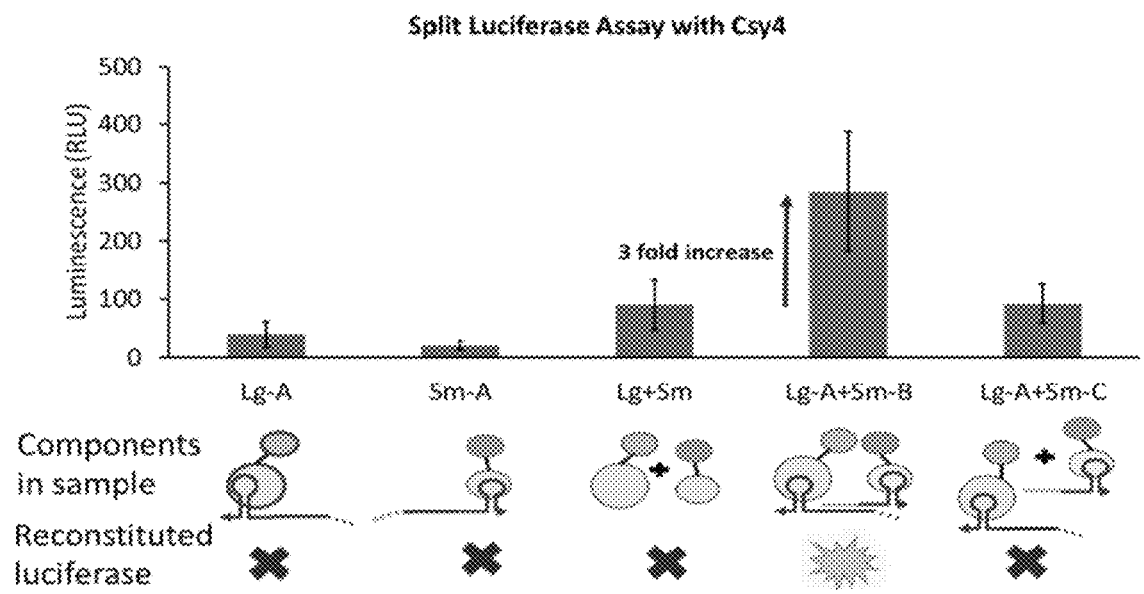
FIG. 6 shows luminescence results in a split luciferase assay for in vitro scaffold assembly in the presence of components: Lg−A, Sm−A, Lg+Sm, Lg−A+Sm−B, or Lg−A+Sm−C.

To test the Cas6-based metabolon assembly, the split nanoluciferase reporter system was used. Recently, a split nanoluciferase was developed to reconstitute active nanoluciferase only upon two fragments, large bit (LgBit) and small bit (SmBit), coming in close proximity through an orthogonal heterodimerization domain (Dixon et al. ACS Chem. Biol. 11:400-8 (2016)). This particular split nanoluciferase was engineered to have a high signal-to-noise ratio, which is highly desirable to determine the dynamic range of the Cas6-based metabolon formation. Using this split nanoluciferase reporter system, the scaffold concept was tested in vitro with two disparate RNA strands in order to determine how the proteins behave on their own, how successfully they are expressed, as well as what the effect of RNA quality and length actually is on the scaffold assembly. For simplicity, the initial in vitro assays were performed with only Csy4 fusions because it is the most characterized Cas6. The LgBit and SmBit domains were fused to the C terminus of the Csy4 protein to generate constructs Csy4-LgBit-his6 (Lg) and Csy4-SmBit-his6 (Sm). Samples comprising scaffold components (1) Csy4-LgBit-his6 bound to RNA strand A (Lg–A), (2) Csy4-SmBit-his6 bound to RNA strand B (Sm–B), (3) Csy4-LgBit-his6 and Csy4-SmBit-his6 (Lg+Sm), (4) Csy4-LgBit-his6 bound to RNA strand A and Csy4-SmBit-his6 bound to RNA strand B (Lg–A+Sm–B), or (5) Csy4-LgBit-his6 bound to RNA strand A and Csy4-SmBit-his6 bound to RNA strand C (Lg–A+Sm–C) were tested. Strands A and B have complementary 5' regions while strands A and C do not have complementary 5' regions. The sample with all of the scaffold components (Lg–A+Sm–B) showed 3.2-fold higher luminescence than the negative control (Lg–A+Sm–C) (FIG. 6), indicating that scaffold assembly occurred due to RNA hybridization, not due to a non-specific interaction. Other controls had similar luminescence to Lg–A+Sm–C (data not shown). The results demonstrate that not only are both the proteins and the RNA strands required for scaffold assembly, but also that the 5' regions of the RNA strands must be complementary.

Example 2. In Vivo Scaffold Assembly

Having demonstrated scaffold assembly specific to the RNA complementary sequences in vitro, the system was tested in vivo next. In the transition, the scaffold RNA sequences were condensed into one large scaffold RNA sequence, a second generation of scaffold RNA. Keeping all of the short sequences for separate expression would require multiple promoter systems (upwards of 4), which would hamper the cells' growth. Condensing all of the scaffold RNA sequences containing orthogonal Cas6 binding motifs, hybridization sequence, and toehold region allows us to place scaffold RNA synthesis under a single promoter. A scaffold was expected to be formed in vivo upon combined expression of the scaffold RNA and orthogonal Cas6 proteins in cells.

Figure 7:
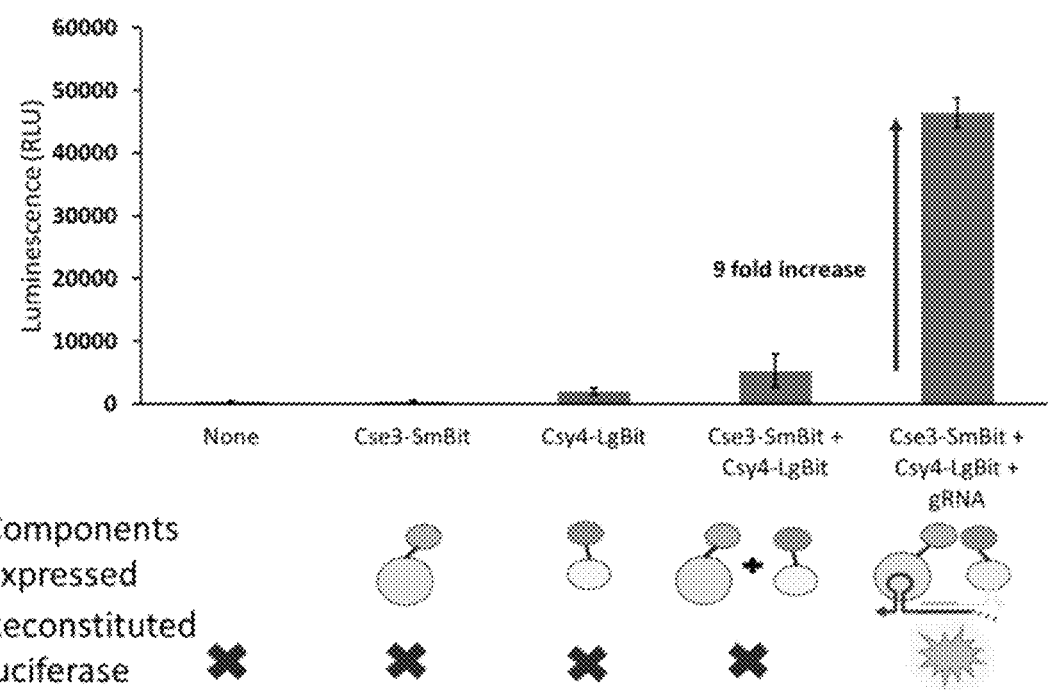
FIG. 7 shows luminescence results in a split luaferase assay for in vivo scaffold assembly in the presence of components: none, Cse3−SmBit, Csy4−LgBit, Cse3−SmBit+Csy4−LgBit, or Cse3−SmBit+Csy4−LgBit+gRNA.

To prevent crosstalk between the two scaffold components, the Csy4 in the SmBit construct was replaced with the orthogonal Cse3 originating from $E.$ $coli$. The corresponding Cse3 binding motif was added to the scaffold RNA strand as well. We hypothesized that Csy4 and Cse3 would be able to bind to and cleave the large RNA strand, thus generating two smaller RNA molecules that would hybridize with each other. The Csy4-LgBit sequence and the RNA sequence having the Csy4 binding motif were combined into one large plasmid through Gibson assembly. The Csy4-LgBit expression was controlled by the lac promoter, the Cse3-SmBit expression was regulated by an arabinose dependent promoter system (araBAD), and the scaffold RNA expression was controlled by the tetracycline dependent (tet) promoter (Rosano and Ceccarelli, $Front.$ $Microbiol.$ 5:1-17 (2014)). BL21 $E.$ $Coli$, co-transformed with both the Csy4-LgBit/scaffold RNA and the Cse3-SmBit plasmids, were grown to an $OD_{600}$ of 0.6-0.8. IPTG induction was achieved by addition of 200 µM IPTG, arabinose induction was achieved by addition of 0.1% w/v arabinose, and tetracycline induction was achieved by addition of 10 ng/µl of anhydrous tetracycline. After induction, the cultures were grown for 4 hours at 30° C. Following the growth period, the $OD_{600}$ of each culture was measured and samples from cultures expressing (1) no scaffold component, (2) Cse3-SmBit, (3) Csy4-LgBit, (4) Cse3-SmBit+Csy4-LgBit, or (5) Cse3-SmBit+Csy4-LgBit+gRNA, which have complementary 5' regions, were taken to normalize each sample's $OD_{600}$ to 2.0. Finally, luminescence was measured using the same technique as for the in vitro assays in Example 1. The sample with all three scaffold components (Cse3-SmBit+Csy4-LgBit+gRNA) showed a 9-fold increase when all three scaffold components were induced as compared with the sample without the gRNA (Cse3-SmBit+Csy4-LgBit) (FIG. 7), confirming the hypothesis that both RNA and Cas6 proteins are required for proper scaffold assembly. This result suggests that small RNA strands that form the dynamic scaffolds not only can be generated in vivo by Cas6 fusion proteins, but they are also able to hybridize to each other as designed in the crowded cellular environment.

An improved expression system was generated to increase the fold increase in luminescence as observed. To help balance the relative levels of Csy4 and Cse3 in the system, the two proteins were placed under the same promoter system, creating a small operon. The protein expression was controlled with the tetracycline inducible system while the RNA expression was controlled by the lac promoter (IPTG induction). For this new and improved system, the assay protocol remained the same except that the induction would occur when the cultures reached an $OD_{600}$ of 1.4 (rather than 0.6-0.8). With this new expression system, we were also able to test functional RNAs with different properties.

Figure 8:
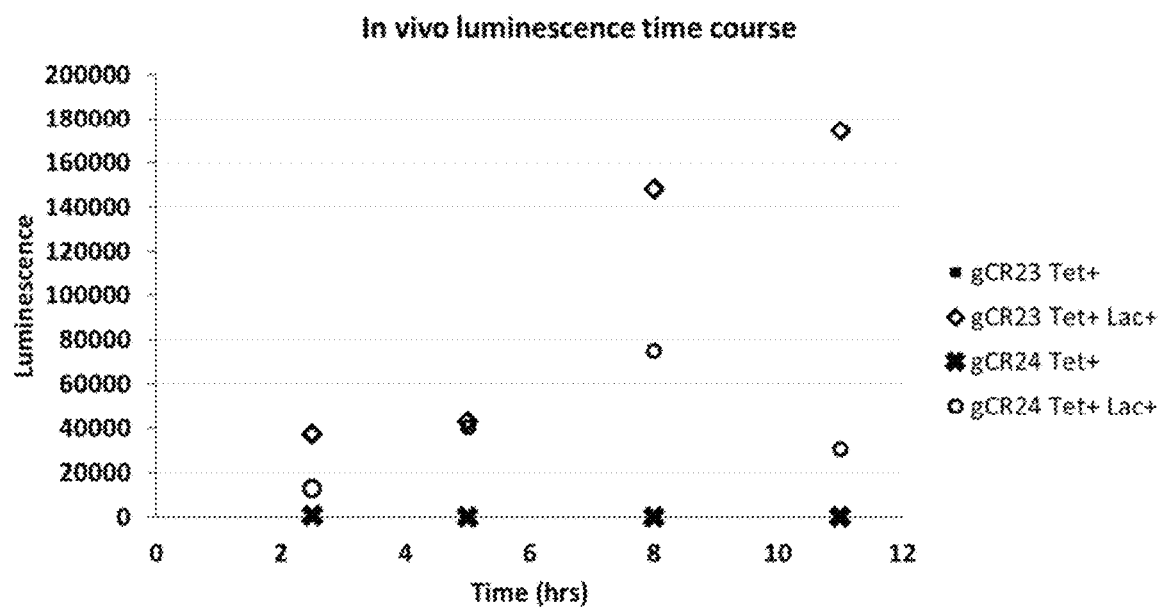
FIG. 8 shows luminescence results in a split luciferase assay for in vivo scaffold assembly in the presence of scaffold RNA gCR23 or gCR24 after induction of protein expression alone (Tet+) or in combination with RNA expression (Tet+Lac+). gCR_23 sequence has complementary 5' regions permitting scaffold assembly. gCR_24 has non complementary 5' hybridization regions prohibiting scaffold assembly.

Two different RNA sequences were tested. The first RNA (gCR23) had 5' hybrdization regions with compatible sequences, which would result in scaffold assembly. The second RNA (gCR24) had 5' hybridization regions with incompatible sequences, also known as scrambled sequences, which would not result in scaffold assembly. Luminescence measurements from samples gCR23 and gCR24 were taken at 2.5, 5, 8 or 11 hours after induction by tetracycline alone (Tet+) or in combination with IPTG induction (Tet+Lac+). The samples with the scrambled 5' hybridization regions (gCR24) showed consistently lower luminescence values than the samples with the compatible 5' hybridization regions (gCR23) (FIG. 8). The scaffold was only assembled when all the scaffold components were expressed and the scaffold RNAs had the appropriate sequences. The fold increase in luminescence was calculated based on the ratio of the luminescence of samples induced for protein expression and scaffold RNA expression (Tet+Lac+) to that of samples induced for protein expression without scaffold RNA expression (Tet+). The maximum fold increase observed in this case was 758.

Figure 9:
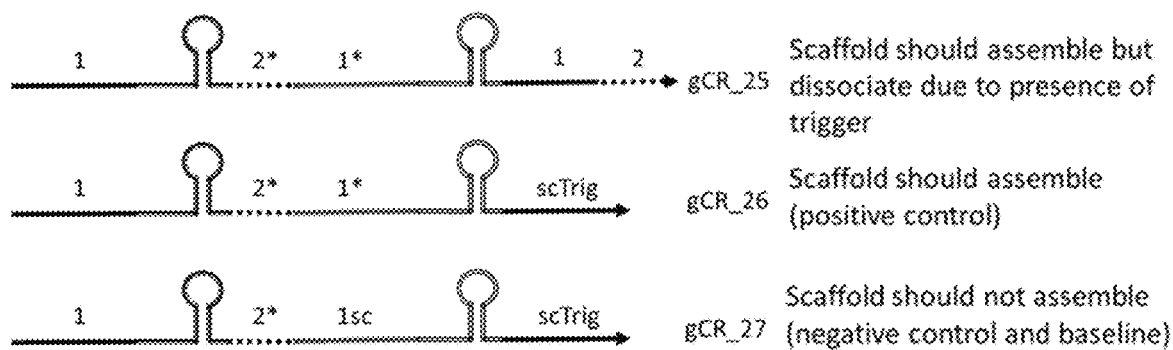
FIG. 9 illustrates scaffold strand gCR_25, gCR_26 and gCR_27 designed for investigation of dissociation of an assembled scaffold in the presence of a trigger strand and reduction of background association.

Example 3. Testing Multiple Scaffold RNAs to Show that the Phenotype of Scaffold Assembly Depends on the RNA Sequences A third generation of scaffold RNAs were prepared and tested. In previous experiments, the toehold region of the scaffold RNA always came first in the overall sequence. In this set of scaffold RNAs, the branch migration region was placed in the middle of the scaffold RNAs. As shown in FIG. 9, three RNA sequences were designed and prepared. The first RNA (gCR25) sequence had compatible 5' hybridization regions 2 and 2* and a toehold region 1*. After the Cse3 cut the scaffold RNA to generate two RNA pieces, a trigger sequence was added to hybridize with the toehold region and displace one of the two RNA pieces. The expected phenotype of gCR25 was scaffold assembly followed by disassembly in the presence of the trigger strand (i.e., constitutive trigger). The second RNA (gCR26) had compatible 5' hybridization regions but a scrambled trigger sequence at the 3' end. After the Cse3 cut the scaffold RNA to generate two RNA pieces, a scrambled trigger sequence was added but could not displace one of the two RNA pieces. The expected phenotype of gCR26 was an assembled scaffold a positive control. The third RNA (gCR27) has incompatible 5's hybridization regions (i.e., scrambled 5' hybridization regions) and a scrambled trigger sequence at the 3' end. The expected phenotype of gCR27 was lack of an assembled scaffold, a negative control.

Figure 10:
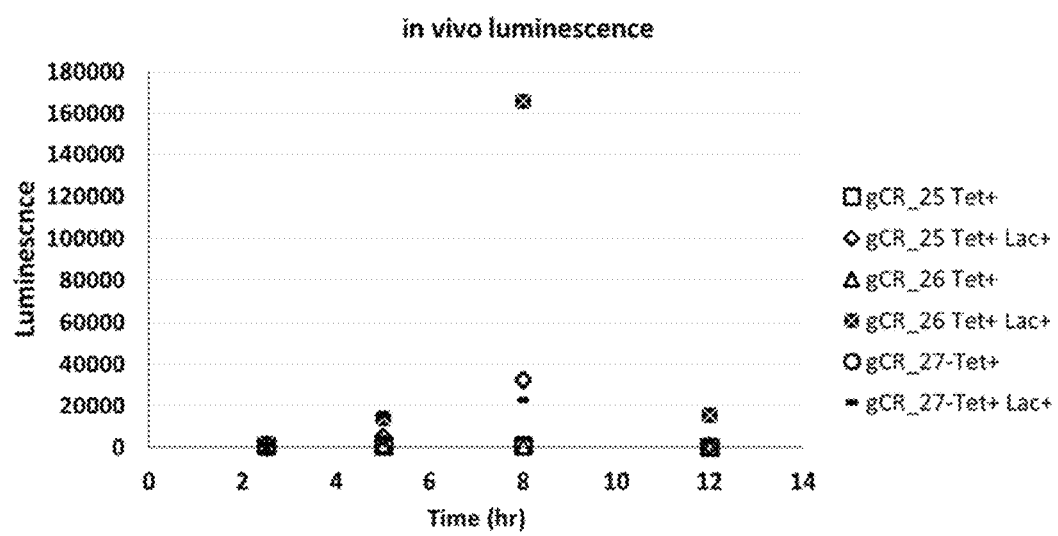
FIG. 10 shows luminescence results in a split luciferase assay for in vivo scaffold assembly in the presence of trigger strand gCR_25, gCR_26 or gCR_27 after induction of protein expression alone (Tet+) or In combination with RNA expression (Tet+Lac+).

This new expression system with the third generation of scaffold RNAs was tested for in vivo luminescence. Luminescence measurements from samples gCR25, gCR26 and gCR27 were taken at 2.5, 5, 8 or 11 hours after induction by tetracycline alone (Tet+) or in combination with IPTG induction (Tet+Lac+). As shown in FIG. 10, gCR27 and gCR26 each showed consistent luminescence values indicating that the phenotypes of gCR27 and gCR26 remained the same over time after induction. The luminescence value of gCR25 increased to the highest level at 8 hours after induction of both protein expression and scaffold RNA expression and then dropped to about the same level as gCR27 11 hours after the induction, demonstrating assembly of scaffold and subsequent disassembly of the assembled scaffold. By testing and comparing these three RNA sequences, we have successfully demonstrated that the scaffold can be assembled and disassembled based on the presence (or lack thereof) of specific RNA sequences in the cellular environment.

Example 4. Impact of Different Spatial Organizations

Figure 11:
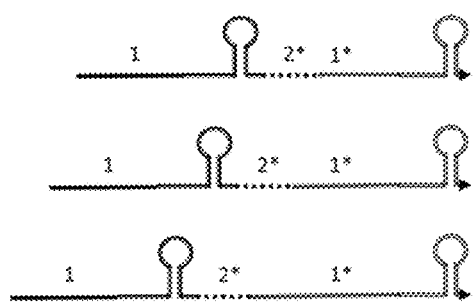
FIG. 11 illustrates scaffold RNA scCR_13, scCR_19 and scCR_26 having different hybridization length.

A fourth generation of scaffold RNAs with different hybridization length (FIG. 11) were generated. The length of the hybridization region was 13 (scCR_13), 19 (scCR_19) or 26 (scCR_26) nucleotides (nt), corresponding 1, 1.5, and 2 helical RNA turns and would position the two proteins of the scaffold in cis, trans, cis orientation. While the 13 and 26 nt hybridization lengths have the same orientation, the two proteins bound to the scaffold RNA would be further apart in the case of the 26 nt length.

Figure 12:
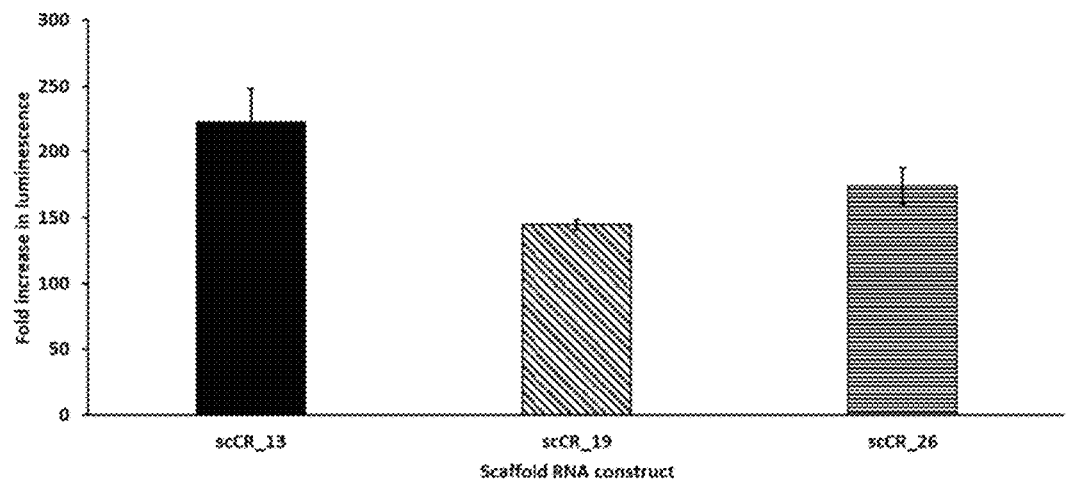
FIG. 12 shows luminescence fold increase results in a split luciferase assay for in vivo scaffold assembly with scCR_13, scC_19 or scCR_26. Fold increase was calculated by taking the ratio of a sample with protein and RNA expression (Tet+Lac+) to a sample with protein induction alone (Tet+)

The new expression system and the fourth generation of scaffold RNAs were used to generate a time course of in vivo luminescence. Luminescence measurements from the samples scCR_13, scCR_19 and scCR_26 were taken at 2.5, 5 or 8 hours after induction. As shown in FIG. 12, the luminescence ratio (i.e., fold increase in luminescence) of samples with scaffold RNA induction to samples without scaffold RNA induction, while proteins were induced in both cases, as measured at the 8-hour point. scCR_13 showed the highest fold increase in luminescence as expected. The sample with the lowest increase in luminescence was scCR_19 indicating that trans configuration while possible, is not ideal for the split luciferase system. Finally, scCR_26 demonstrated the second highest luminescence, Indicating that the most important aspect in our system is the cis orientation of proteins, followed by the actual length separating the two proteins of interest. While the optimal configuration for the split luciferase system is scCR_13, the remaining two configurations could prove useful when applying the scaffold in different settings. gCR_26 is an optimal scaffold RNA because it minimizes background or non-specific protein association while still retaining good activation.

Example 5. Dissociation of Scaffold on Cue by Induction of a Trigger Strand (Turn OFF System)

A Turn OFF system, i.e., disassembly of an assembled scaffold on cue of a trigger strand, has been demonstrated using the optimal scaffold RNA (gCR_26) and an independent trigger strand. The independent trigger strand was under an induction system different from that for the scaffold RNA molecules. To achieve this, the trigger sequence was placed under the control of a separate induction system, controlled by the addition of arabinose to the cell culture. The trigger strand expression was induced 2.5 hours after induction of the protein and scaffold RNA. To measure the efficiency of the trigger, two separate trigger constructs were generated, a regular trigger (R-T), which was expected to successfully dissociate the scaffold complex formed upon induction, and a scrambled toehold trigger (ScTh-T), which had a scrambled toehold region and was therefore expected not to initiate the toehold mediated strand displacement reaction necessary for successful scaffold dissociation. A fully scrambled trigger (FSc-T) was expected to bind neither to the toehold region nor the hybridization region. The system was tested using the split luciferase reporter system as described in Examples 1-4.

Figure 13:
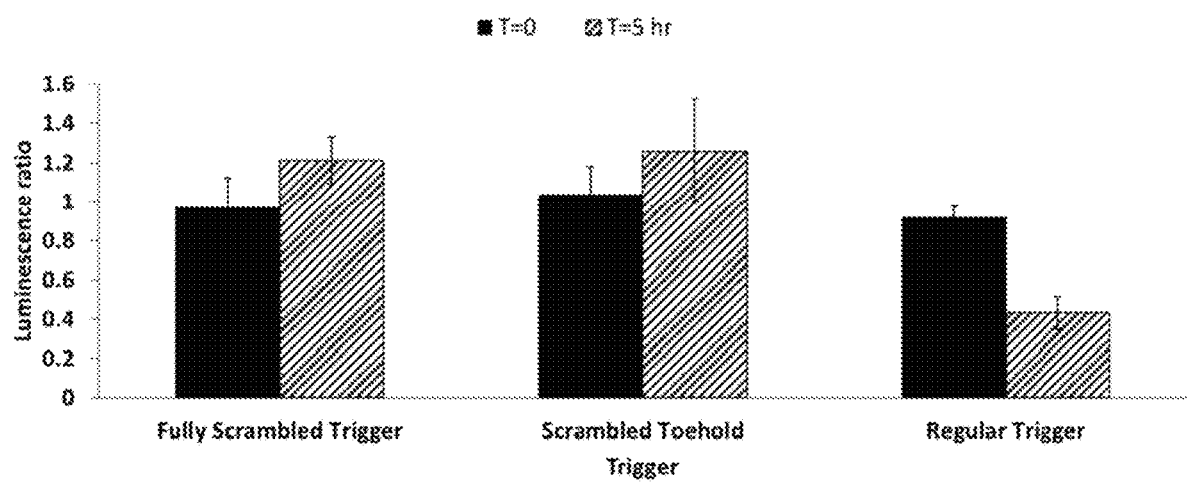
FIG. 13 shows luminescence ratios in a split luciferase assay for in vivo scaffold disassembly upon induction of a fully scrambled trigger, a scrambled toehold trigger or a regular trigger.

The results illustrated in FIG. 13 indicate that the scaffold was successfully dissociated upon induction of the trigger strand. The bar graphs for each sample demonstrate the luminescence ratio between a sample with scaffold RNA, proteins, and trigger strand induced to a sample with scaffold RNA and proteins. The bar graph at T=0 indicates the ratio at the time the trigger strand was induced. The bar graph at T=5 indicates the ratio 5 hours after the trigger was induced. For the ScTh-T and the FSc-T, the ratio at both time points hovered around 1, Indicating that the presence of a partial or fully scrambled trigger did not result in scaffold dissociation. On the other hand, the ratio for R-T dropped from 1.4 to around 0.45 indicating successful dissociation of the scaffold in the presence of a regular trigger. This new configuration and controls have successfully demonstrated that the scaffold can be dissociated on command by the expression of an independent trigger strand.

Example 6. Assembly of Scaffold Via Expression of a Toehold Strand (Turn ON System)

A Turn ON system, i.e., assembly of a scaffold on cue of a toehold strand, has been demonstrated by adding a trigger strand to an assembled scaffold. Two RNA molecules containing binding hairpins for orthogonal Cas6 proteins Cse3 and Csy4 were expressed separately. Initially, the two RNA strands with the proteins of interest bound to them were unable to hybridize with each other because one of the two hybridization sequences was blocked by design (FIG. 14a). Upon addition of a trigger strand, through toehold mediated strand displacement, the blocked region became unblocked (FIG. 14b). With the two complementary hybridization regions now unlocked, the two RNA molecules associated with each other, thus colocalizing the two enzymes of interest E1 and E2 (FIG. 14c).

To demonstrate that scaffold association only occurs in the presence of a correct trigger RNA sequence, three different sequences for the trigger RNA were tested. A regular trigger (R-T) would turn the system ON, i.e., scaffold assembly. The scrambled toehold sequence (ScTh) would only turn the system on if there were significant competition between the blocked strand and the trigger. Finally, the fully scrambled trigger (FSc) would not turn the system on in any case.

Figure 16:
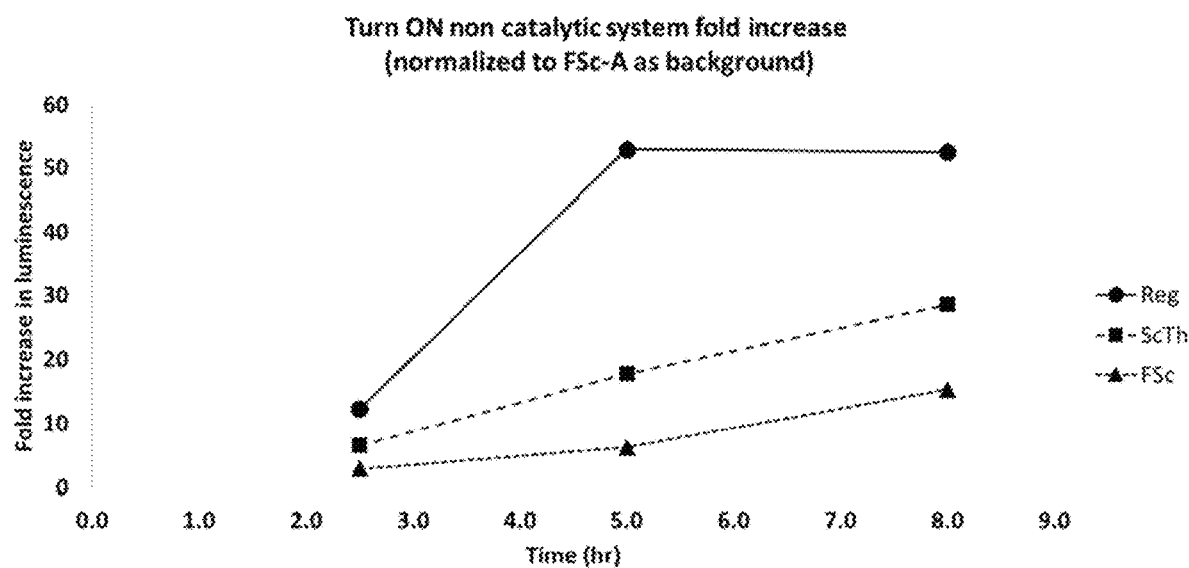
FIG. 16 shows fold increase in luminescence in a split luciferase assay for a Turn ON non catalytic system upon induction of a regular trigger (Reg), a scrambled toehold trigger (ScTh) and a fully scrambled trigger (FSc).

Samples induced by one of the three triggers of FIG. 15 and samples not induced by a trigger were tested for fold increase in luminescence. Due to some trigger leakage, all of the fold changes were normalized to the sample with the fully scrambled trigger (i.e., without trigger induction). As shown in FIG. 16, our Turn ON RNA configuration only demonstrates significant protein association in the presence of the correct RNA trigger sequence. This new configuration and controls have successfully demonstrated that scaffold assembly can be controlled by the expression of an independent trigger strand.

Example 7. Increasing Production of Indole-3-Acetic Acid (IAA)

IAA is a plant growth regulator, which can be produced in E. coli using a two-step enzymatic pathway. The pathway uses tryptophan as a substrate, and with the help of enzymes IaaM and IaaH converts tryptophan to indole-3-acetic acid. To test the functionality of our scaffold, the pathway enzymes were fused to two orthogonal Cas6 proteins, thus creating novel protein fusions Csy4-IaaM and Cse3-IaaH.

Figure 17:
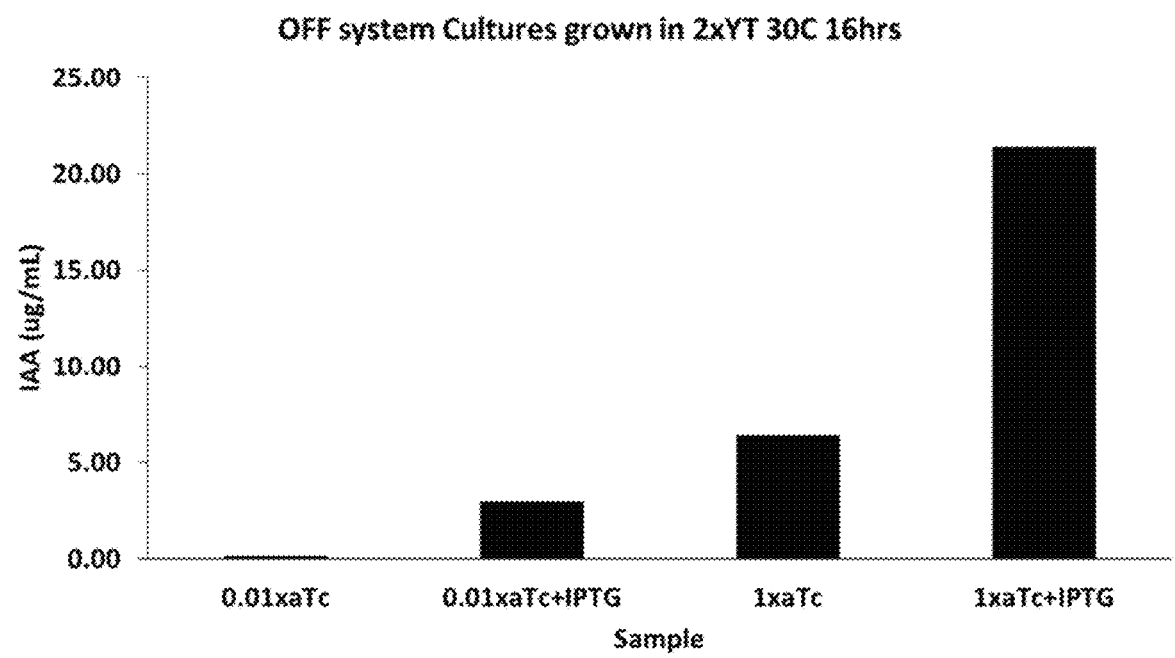
FIG. 17 shows IAA concentration in OFF system cultures upon induction of protein expression alone (0.01×aTc or 1×aTc) or in combination with RNA expression (0.01×aTc+IPTG or 1×aTc+IPTG).

FIG. 17 illustrates that a Turn OFF system can be used to successfully increase the product titer of a two-step metabolic pathway through scaffolding of two pathway enzymes. The two protein fusions Csy4-IaaM and Cse3-IaaH were expressed together with scaffold RNA construct gCR_26 in the same manner as the original split luciferase constructs. The level of IAA produced was assayed using high performance liquid chromatography (HPLC). Protein induction was controlled by a Tet promoter (aTc) whereas scaffold RNA expression was controlled by a lac promoter (IPTG). Two different induction strengths of the proteins were tested (0.01×aTc and 1×aTc). The low protein induction was achieved by using 100-fold less of the inducer aTc. In the case of the sample 0.01×aTc, there was no peak observed in the HPLC graph hence the value was set to 0. The fold change was greater in the case of the low protein induction (0.01×aTc); however the highest product titer was achieved with the high protein induction (1×aTc).

Figure 18:
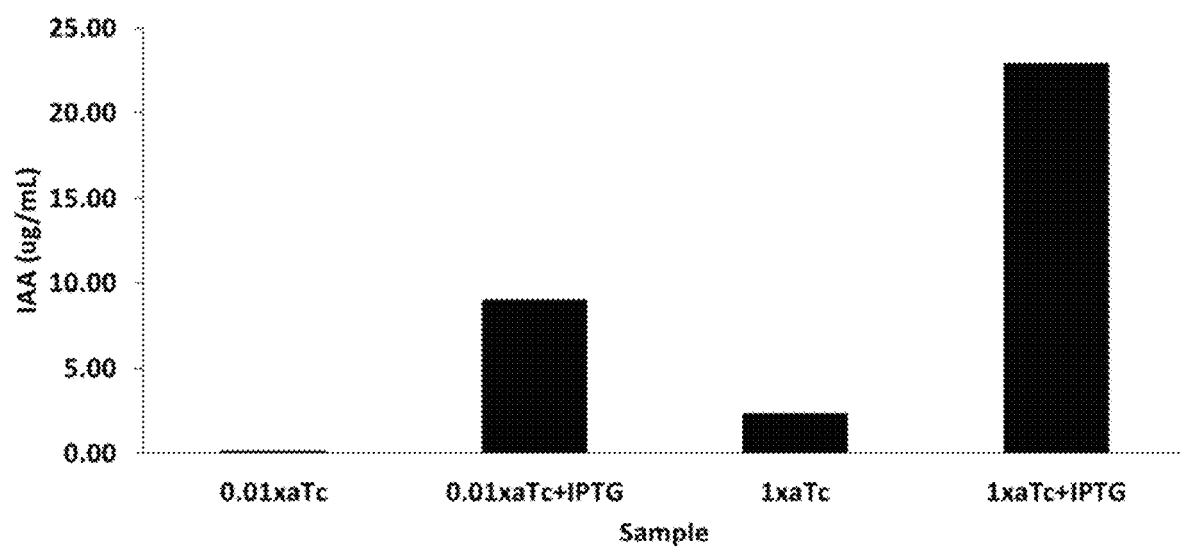
FIG. 18 shows IAA concentration in ON system cultures upon induction of protein expression alone (0.01×aTc or 1×aTc) or in combination with RNA expression (0.01×aTc+IPTG or 1×aTc+IPTG).

FIG. 18 illustrates that a Turn ON system can also be used to successfully increase the product titer of a two-step metabolic pathway through scaffolding of two pathway enzymes. The induction scheme and approach for measuring final product are the same as in FIG. 17. The only difference now is that gCR_26 was substituted by the Turn ON system. For the Turn ON system, the two scaffold hairpins were expressed through a constitutive synthetic promoter, and the trigger that led to scaffold assembly was induced through IPTG addition. Again, two different induction strengths were tested for the protein expression. The results in this figure illustrates that the Turn ON system can also be used to successfully increase the product titer of a two-step metabolic pathway through scaffolding of the two pathway enzymes. The fold change was greater in the case of the low protein induction (0.01×aTc); however the highest product titer was achieved with the high protein induction (1×aTc). In the case of the Turn ON system, the max product titer was slightly lower than that of the Turn OFF (gCR_26) system, however the fold increase of product was higher between the two samples 1×aTc and 1×aTc+IPTG. This means that the Turn ON system allows for more stringent control of the pathway flux at the tradeoff of slightly lower final product titer.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A method for controlling colocalization of a first heterologous protein with a second heterologous protein in a cell, comprising:
  (a) expressing the first heterologous protein and a first scaffold RNA molecule in the cell, wherein the first scaffold RNA molecule comprises a first binding motif, a hybridization sequence and a toehold sequence, the first heterologous protein is bound to the first binding motif, and the hybridization sequence is bound to a first sequence complementary with the hybridization sequence;

(b) expressing the second heterologous protein and a second scaffold RNA molecule in the cell, wherein
the second scaffold RNA molecule comprises a second binding motif and the first sequence complementary with the hybridization sequence, the second heterologous protein is bound to the second binding motif, whereby the first heterologous protein is colocalized with the second heterologous protein in the cell;
(c) expressing a trigger RNA molecule in the cell, wherein the trigger RNA molecule comprises a first trigger sequence complementary with the toehold sequence and a second trigger sequence complementary with the hybridization sequence,
(d) binding the first trigger sequence complementary with the toehold sequence to the toehold sequence and binding the second trigger sequence complementary with the hybridization sequence to the hybridization sequence whereby the first sequence complementary with the hybridization sequence is separated from the hybridization sequence and the first heterologous protein is not colocalized with the second heterologous protein in the cell.

2. The method of claim 1, wherein the first heterologous protein and the second heterologous protein are different, and the first binding motif and the second binding motif are different.

3. The method of claim 2, wherein the first heterologous protein and the second heterologous protein are expressed under the same promoter.

4. The method of claim 1, wherein each of the first binding motif and the second binding motif has a hairpin sequence.

5. The method of claim 4, wherein the hairpin sequence consists of 25-35 nucleotides.

6. The method of claim 4, wherein the hairpin sequence consists of 30 nucleotides.

7. The method of claim 1, wherein the cell is selected from the group consisting of E. coli, S. cerevisiae, and HeLa cells.

8. The method of claim 1, further comprising expressing a combined scaffold RNA molecule in the cell, and cleaving the combined scaffold RNA to generate the first scaffold RNA molecule and the second scaffold RNA molecule in the cell.

9. The method of claim 1, further comprising expressing a third heterologous protein and a third scaffold RNA molecule in the cell, wherein the third scaffold RNA molecule comprises a third binding motif and a third sequence consisting of a polynucleotide sequence identical to that of the hybridization sequence, and the third heterologous protein is bound to the third binding motif, whereby the first sequence complementary with the hybridization sequence is bound to the third sequence consisting of a polynucleotide sequence identical to that of the hybridization sequence, and the second heterologous protein is colocalized with the third heterologous protein.

10. A method for controlling colocalization of a first heterologous protein with a second heterologous protein in a cell, comprising:
(a) expressing the first heterologous protein and a first scaffold RNA molecule in the cell, wherein the first scaffold RNA molecule comprises a first binding motif, a hybridization sequence, a first sequence complementary with the hybridization sequence and a toehold sequence, the first heterologous protein is bound to the first binding motif, and the hybridization sequence is bound to the first sequence complementary with the hybridization sequence;
(b) expressing the second heterologous protein and a second scaffold RNA molecule in the cell, wherein the second scaffold RNA molecule comprises a second binding motif and a second sequence consisting of a polynucleotide sequence identical to the hybridization sequence, the second heterologous protein is bound to the second binding motif, whereby the first heterologous protein is not colocalized with the second heterologous protein in the cell;
(c) expressing a trigger RNA molecule in the cell, wherein the trigger RNA molecule comprises a first trigger sequence complementary with the toehold sequence and a second trigger sequence complementary with the hybridization sequence,
(d) binding the first trigger sequence complementary with the toehold sequence to the toehold sequence, whereby the first sequence complementary with the hybridization sequence is separated from the hybridization sequence, and
(e) binding the second trigger sequence complementary with the hybridization sequence to the hybridization sequence, whereby the second sequence consisting of a polynucleotide sequence identical to that of the hybridization sequence is bound to the first sequence complementary with the hybridization sequence, and the first heterologous protein is colocalized with the second heterologous protein in the cell.

11. The method of claim 1, wherein the first heterologous protein and the second heterologous protein provide a biological activity in the cell when the first heterologous protein is colocalized with the second heterologous protein, and the biological activity is reduced when the first heterologous protein is not colocalized with the second heterologous protein.

12. The method of claim 1, wherein the first heterologous protein and the second heterologous protein provide a biological activity in the cell when the first heterologous protein is not colocalized with the second heterologous protein, and the biological activity is reduced when the first heterologous protein is colocalized with the second heterologous protein.

13. The method of claim 1, wherein the first heterologous protein is a first fusion protein of a first enzyme and a first binding protein capable of binding to the first binding motif, and the second heterologous protein is a second fusion protein of a second enzyme and a second binding protein capable of binding to the second binding motif, wherein the first enzyme and the second enzyme provide a biological activity in the cell when the first heterologous protein is colocalized with the second heterologous protein, and the biological activity is reduced when the first heterologous protein is not colocalized with the second heterologous protein.

14. The method of claim 1, wherein the first heterologous protein is a first fusion protein of a first enzyme and a first binding protein capable of binding to the first binding motif, and the second heterologous protein is a second fusion protein of a second enzyme and a second binding protein capable of binding to the second binding motif, wherein the first enzyme and the second enzyme provide a biological activity in the cell when the first heterologous protein is not colocalized with the second heterologous protein, and the biological activity is reduced when the first heterologous protein is colocalized with the second heterologous protein.

15. The method of claim 13, wherein each of the first binding protein and the second binding protein is selected from the group consisting of Csy4 from *P. aeruginosa*, Cse3 from *E. coli*, Cse3 from *T. thermophilus*, and Cas6 from *P. furiosus*.

16. The method of claim 13, wherein the cell produces a metabolite, and wherein the production of the metabolite by the cell is increased when the first heterologous protein and the second heterologous protein are colocalized and reduced when the first heterologous protein and the second heterologous protein are separated.

17. The method of claim 14, wherein the cell produces a metabolite, and wherein the production of the metabolite by the cell is increased when the first heterologous protein and the second heterologous protein are colocalized and reduced when the first heterologous protein and the second heterologous protein are separated.

18. The method of claim 16, wherein the metabolite is selected from the group consisting of indole-3-acetic acid, trans-resveratrol, and violacein.

19. The method of claim 16, wherein each of the first enzyme and the second enzyme is selected from the group consisting of Tryptophan-2-monooxygenase (IaaM), Indoleacetamide hydrolase (IaaH), 4-coumarate ligase (4CL), Stilbene synthase (STS), Violacein synthase (VioC), Protodeoxyviolaceinate monooxygenase (VioD), and Violacein biosynthesis protein VioE.

20. The method of claim 10, wherein the first heterologous protein and the second heterologous protein are different, and the first binding motif and the second binding motif are different.

* * * * *

SEQUENCE LISTING

<160> NUMBER OF SEQ ID NOS: 3

<210> SEQ ID NO 1
<211> LENGTH: 28
<212> TYPE: DNA
<213> ORGANISM: Artificial Sequence
<220> FEATURE:
<223> OTHER INFORMATION: Synthetic

<400> SEQUENCE: 1
gttcactgcc gtataggcag ctaagaaa         28

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
gagttccccg cgccagcggg gattaaaccg         30

<210> SEQ ID NO 3
<211> LENGTH: 36
<212> TYPE: DNA
<213> ORGANISM: Artificial Sequence
<220> FEATURE:
<223> OTHER INFORMATION: Synthetic

<400> SEQUENCE: 3
ggatcgatac caccccgaag aaaaggggac gagaac         36